United States Patent
Frings (10) Patent No.: US 9,848,897 B2
(45) Date of Patent: Dec. 26, 2017

(54) MEDICAL INSTRUMENT WITH A FLEXIBLE TOOTHED BELT

(71) Applicant: Karl Storz SE & Co. KG, Tuttlingen (DE)

(72) Inventor: Hermann-Josef Frings, Aachen (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 194 days.

(21) Appl. No.: 14/576,526

(22) Filed: Dec. 19, 2014

(65) Prior Publication Data

US 2015/0173787 A1 Jun. 25, 2015

(30) Foreign Application Priority Data

Dec. 19, 2013 (DE) .................. 10 2013 114 557

(51) Int. Cl.
*A61B 17/00* (2006.01)
*A61B 17/28* (2006.01)
(Continued)

(52) U.S. Cl.
CPC ........ *A61B 17/2816* (2013.01); *A61B 17/282* (2013.01); *A61B 17/29* (2013.01);
(Continued)

(58) Field of Classification Search
CPC .............. A61B 17/2816; A61B 17/282; A61B 17/3201; A61B 2017/2902;
(Continued)

(56) References Cited

U.S. PATENT DOCUMENTS 5,792,165 A * 8/1998 Klieman ............... A61B 17/29
606/170
5,827,323 A * 10/1998 Klieman ............... A61B 17/29
606/170
(Continued)

FOREIGN PATENT DOCUMENTS

| DE | 102012220578 A1 | 5/2014 |
| EP | 2412318 A2 | 2/2012 |
| JP | S63176092 U | 11/1988 |

OTHER PUBLICATIONS

United Kingdom Search Report Application No. GB1422043.8 Completed: May 5, 2015; dated May 6, 2015 3 pages.

*Primary Examiner* — Diane Yabut
*Assistant Examiner* — Martin T Ton
(74) *Attorney, Agent, or Firm* — Whitmyer IP Group LLC (57) ABSTRACT

A medical instrument has a shaft with a longitudinal axis, a jaw head on a distal end of the shaft having two jaw parts, at least one of the jaw parts being pivotable about a pivot axis extending transversely to the longitudinal axis, the pivotable jaw part having a wheel portion with toothing mounted about the pivot axis, at least one actuation element having a distal end portion with toothing that meshes with the toothing of the wheel portion such that movement of the actuation element along the longitudinal axis pivots the pivotable jaw part, control elements at a proximal end of the shaft controlling movement of the actuation element, said distal end portion with toothing is flexible, one of the jaws having a hollow space arranged distally to the pivot axis, wherein the distal end portion comes in or out of the hollow space when moving the actuation element.

21 Claims, 5 Drawing Sheets

(51) Int. Cl.
*A61B 17/3201* (2006.01)
*A61B 17/29* (2006.01)
A61B 17/24 (2006.01)
A61B 17/32 (2006.01)

(52) U.S. Cl.
CPC .......... *A61B 17/3201* (2013.01); *A61B 17/24* (2013.01); *A61B 2017/00398* (2013.01); *A61B 2017/2902* (2013.01); *A61B 2017/294* (2013.01); *A61B 2017/2911* (2013.01); *A61B 2017/2927* (2013.01); *A61B 2017/2943* (2013.01); *A61B 2017/320044* (2013.01)

(58) Field of Classification Search
CPC .... A61B 2017/2903; A61B 2017/2905; A61B 2017/2926; A61B 2017/2927; A61B 2017/2939; A61B 2017/2943; A61B 2017/294; A61B 2017/2944; A61B 2017/2825; A61B 2017/2829; A61B 2017/293; A61B 2017/2932; A61B 2017/2933; A61B 2017/2934; A61B 2017/2936; A61B 2017/2937; A61B 2017/2938
USPC .......................................... 606/205, 207, 208
See application file for complete search history.

(56) References Cited

U.S. PATENT DOCUMENTS 9,498,281 B2 * 11/2016 Kendrick ............... A61B 17/29
2003/0100892 A1   5/2003 Morley et al.
2011/0276084 A1 * 11/2011 Shelton, IV ........... A61B 17/29
                                                                606/205

\* cited by examiner

MEDICAL INSTRUMENT WITH A FLEXIBLE TOOTHED BELT

BACKGROUND OF THE INVENTION

The invention relates to a medical instrument with a shaft which has a distal end and a proximal end, with a jaw head, which is arranged on the distal end and has two jaw parts, of which at least one is pivotable.

An instrument of this kind in the form of a medical forceps is known from U.S. Pat. No. 5,827,323. Both jaw parts are movable and are mounted pivotably about a common axis at the distal end of the shaft. Each of the jaw parts has a toothed wheel portion arranged concentrically around the pivot axis. This toothed wheel portion meshes with a toothed distal end of a rectilinearly extending stiff actuation element. Thus, an elongate rod-shaped actuation element is present in the shaft for each jaw part, said actuation element being provided with a corresponding toothing on the side facing towards the toothed wheel portion of the jaw part. Thus, when one of the actuation elements is moved axially to and fro in the shaft, this movement is converted via the toothed engagement into a pivoting movement of a jaw part.

The toothing or meshing is configured such that the toothed wheel portion of a jaw part, when the latter is oriented approximately linearly with the shaft, is in engagement with the outermost distal end of the toothed wheel portion. If this actuation element is now moved in the distal direction, the jaw part pivots out from the linear orientation with the shaft, or with the central longitudinal axis of the latter, and is thus opened.

A disadvantage is that the distally advancing linear end portion extends more and more distally beyond the toothed wheel portion the further the jaw part is pivoted. These distally advanced end portions therefore occupy a considerable space distally in front of the articulation area of the pivotable jaw parts. In the final analysis, a pointed structure results, which is formed by the two distal end portions of the actuation elements provided with the toothing.

If such forceps are to be inserted into body cavities that are narrow or difficult to access, this "point" formed by the distally protruding distal end portions gets in the way. A possible area of use lies in the area of the frontal sinuses. There, a forceps-like instrument of this kind is pushed into the nasal opening initially with a rectilinear orientation of the jaw parts, after which the latter are introduced into the paranasal sinus or frontal sinus through an aperture, a so-called window. The space available there is small, especially in children for example, such that there is already little room for manoeuvre of the pivotable jaw parts. If the person operating this instrument wishes to work with the jaw parts pivoted out far to the sides, a relatively long "point" juts out in the direction of the longitudinal axis of the shaft, which "point" is formed by the advanced distal end portions of the actuation elements.

This makes the manipulation awkward.

US 2003/0100892 A1 discloses to pivot the jaw head and the jaw parts via cable pulls. However, very complicated structures are needed, namely a large number of cables and pulleys for controlling the different pivoting movements. Since considerable forces have to be applied to the jaw parts when separating tissue, for example cartilage, it is necessary to guide the cables with a high degree of tensioning around the pulleys of the cable pulls to ensure that they do not slip. If, as has already been mentioned, devices of this kind are intended to be used where there is little space available, they have to be made correspondingly slim, and therefore elaborate cable pull mechanisms of this kind are bulky and cannot have the required stability. In addition, complicated movement mechanisms of this kind are difficult to clean.

It is therefore an object of the present invention to further develop a medical instrument of the type mentioned at the outset in such a way that, with a control system that is as simple as possible and takes up little space, it is possible to achieve a high degree of flexibility and numerous degrees of freedom of movement of jaw head and jaw parts.

SUMMARY OF THE INVENTION

This object is achieved by a medical instrument comprising a shaft having a distal end, a proximal end and a longitudinal axis, a jaw head arranged on said distal end of said shaft, said jaw head having two jaw parts, at least one of said two jaw parts being pivotable about a pivot axis extending transversely to said shaft axis, said at least one pivotable jaw part having a wheel portion mounted about said pivot axis, said wheel portion having a toothing, at least one actuation element for pivoting said at least one pivotable jaw part, said actuation element having a distal end portion provided with a toothing, said toothing of said actuation element meshes with said toothing of said wheel portion in such a way that an axial movement of said actuation element along said longitudinal axis of said shaft pivots said pivotable jaw part, and control elements arranged at said proximal end of said shaft, said control elements controlling a movement of said at least one actuation element, wherein said distal end portion of said actuation element provided with said toothing is made flexible, and at least one of said two jaws having a hollow space arranged distally to said pivot axis, and wherein said flexible distal end portion of said actuation elements comes in or comes out of said hollow space when moving said actuation element along said shaft axis to distal and to proximal respectively.

The provision of a hollow space in a jaw part in which the flexible end portion of the actuation element can be driven in and out affords the possibility that no large space is needed around the jaw part into which the flexible portion can be brought. This hollow space can be a cavity or a groove which is cut in from the outside and in which the flexible end portion moves in and out during the movement of the actuation element. With the groove, suitable precautions then have to be taken, for example corresponding webs covering the groove, which ensure that the flexible end portion with the toothing on the one hand follows the pivoting movements of the jaw part and on the other hand has sufficient space in the longitudinal direction of the jaw part in order to move along the jaw part. If the jaw head has a pivotable and stationary jaw part, the flexible toothed end portion can be accommodated either in the pivotable or in the stationary jaw part. If accommodated in the pivotable jaw part, the flexible toothed end portion located distally to the pivot axis can follow the pivot movements of the jaw pivotable part.

In a further embodiment of the invention, the hollow space has a proximal opening through which the distal end portion of the actuation element with the toothing can be driven in and out of this hollow space.

This measure has the advantage that the toothed flexible end portion moves into the interior of the jaw part and is thus unaffected by external influences and also requires no installation space around the jaw part.

In a further embodiment of the invention, the hollow space is designed such that it completely encloses the distal flexible end portion except for the opening which said distal flexible end portion enters.

The flexible end portion is in this way protected against external influences. These can be mechanical effects or contamination.

In a further embodiment of the invention, the distal end portion can be driven in and out of a hollow space formed in the jaw part that can be pivoted by the toothed end portion.

This measure has the advantage that the flexible end portion can be arranged as directly as possible on the jaw part that it moves and can be driven in and out of this jaw part.

This also has the advantage that the operator receives direct feedback via the control element that moves the corresponding jaw part. In other words, when the operator moves a control element, he or she knows which actuation element is thereby moved, and knows that precisely this actuation element moves a specific jaw part and also moves in and out of the latter.

In a further embodiment of the invention, the distal end portion can be driven in and out of a hollow space formed in the respective other jaw part that is not pivoted by this distal end portion.

If there are two pivotable jaw parts, there is on each of these a toothed wheel portion which meshes with a respective flexible end portion of one of the two actuation elements. It has been found here that it may be expedient in design terms to allow the flexible end portion to be driven into the respective other jaw part.

This also depends on which of the two jaw parts is possibly the more stable, in so far as they are not identical in mirror image, and on which of the jaw parts is intended to perform a closure movement. The forces for opening and closing the jaw parts have to be transmitted to the latter by the flexible end portion with the toothing. Since much less force has to be transmitted when opening a jaw part than when closing a jaw part, for example in order to separate a piece of tissue or cartilage, it may be more expedient to apply these forces by pulling on the toothed end portion and not pushing it. This then means that, with the jaw part opened, the flexible end portion has to be driven quite far or even all the way into the inner hollow space. By pulling on the actuation element, i.e. moving it in the proximal direction, the force can be better exerted and transmitted, in order to close this pivotable jaw part. However, if the other jaw part is the larger one for structural reasons, it may be expedient not to drive this flexible toothed end portion into the jaw part that is moved by this flexible toothed end portion, but instead into another, possibly larger or more favourably located jaw part.

In a further embodiment of the invention, the jaw head has a stationary jaw part and a pivotable jaw part, with the hollow space being formed in the stationary jaw part.

This is a practical instance of the possibility discussed above. In many jaw heads, particularly in those with a stationary jaw part, the latter is often more stable or larger than the jaw part that is pivotable towards or away from it.

It may then be expedient here in design terms if the actuation element operatively connected to the pivotable jaw part can be connected only to the toothed wheel portion thereof. However, the portion that advances during the movement can then be driven into the other jaw part, here the stationary jaw part. This allows the designer to react in a very flexible way to given structural measures or to the demands surrounding the use of such a medical instrument.

In a further embodiment, the toothed wheel portion of the jaw part is designed as a toothed wheel with external toothing, which toothed wheel is mounted on a journal about which the jaw part is pivotable.

This measure has the advantage that the size and in particular the diameter of the toothed wheel can determine the torque that can or should be transmitted.

The toothed wheel can be mounted laterally or level with the height of the body of the jaw part. In this way, the flexible end portion of the actuation element can then be driven safely and deliberately in and out of a hollow space in this jaw part or, in the case of lateral arrangement, a hollow space on the other jaw part.

In a further embodiment of the invention, the toothed wheel is mounted in such a way that it is integrated as fully as possible in the respective jaw part.

This measure has the advantage that the respective toothed wheel is covered towards the outside by the jaw part.

In a further embodiment of the invention, the jaw head has two pivotable jaw parts, each of which jaw parts is connected to a separate actuation element, such that the jaw parts can be opened and closed individually and are also movable at the same time for pivoting the entire jaw head.

This measure increases the degree of freedom in the sense that, with two jaw parts, it is possible for these to be movable in different ways. Thus, both can be pivoted in the same direction such that, in the final analysis, the entire jaw head is then pivoted. However, both can also be opened and closed independently of each other, such that opening and closing movements can be carried out from any desired pivoting positions of the jaw head.

In a further embodiment of the invention, the two actuation elements are accommodated in the shaft in a manner arranged coaxially with respect to each other.

This measure has the considerable advantage that a very slender structure can result from it.

In a particularly advantageous embodiment in this connection, the actuation elements are designed as two tubular bodies which are pushed one inside the other in the shaft.

In a further embodiment of the invention, each actuation element is provided at the proximal end of the shaft with a control element.

This measure known per se has the advantage that the movements of the actuation elements, hence of the jaw parts, can be carried out independently of each other by ergonomically situated control elements.

In a further embodiment, the control elements are grip parts with finger eyelets.

This measure has the advantage that the control elements concerned are elements which are common in the medical sector and familiar to the operator and are used for moving actuation elements in medical forceps or scissors.

In a further embodiment of the invention, a handle is arranged at the proximal end of the shaft.

This measure has the advantage that, in medical instruments with an actuation element, the latter can be easily and safely moved using simple and customary features or structural parts.

In a further embodiment of the invention, the grip parts are arranged at the proximal end area of the shaft.

This measure has the advantage that, with the provision of two pivotable jaw parts having two actuation elements, the latter can each be moved simply and ergonomically via the corresponding movable grip parts.

In a further embodiment of the invention, the one actuation element or both actuation elements are accommodated in the shaft in such a way that they are rotatable about the longitudinal axis of the shaft.

This measure has the advantage that manipulation is increased by a further degree of freedom, namely that the jaw head with its two jaw parts is also pivotable about the longitudinal axis of the shaft. For example, a shaft can be introduced into a maxillary sinus and, by rotating the actuation elements about the shaft axis, the jaw head can first of all be brought to a favourable position of rotation, from which the separation procedures can then be performed with the jaw head pivoted laterally.

In a further embodiment of the invention, the control elements at the proximal end and the shaft are rotatable relative to each other about the shaft axis.

This further extends the degree of freedom of manipulation in the sense that the control elements at the proximal end, and of course also the actuation elements connected to them, and the jaw parts are rotatable relative to the shaft.

In a further embodiment of the invention, the control elements are designed as motorized drives which are arranged at the proximal end and are used for moving the actuation elements axially to and fro and optionally in rotation.

This measure has the advantage that the movements of the actuation elements can be performed in a controlled manner by motor. This can easily be achieved, for example, if both the first actuation element and also the second actuation element are provided at their proximal end area with corresponding linear drives that can be actuated via control elements. A further drive, namely a rotary drive, can then be provided in order to effect the rotation of the actuation elements. This entire drive can be offered to the operator as a handle on which, for example, the control elements appear as corresponding function buttons via which, for example by symbols, colour markings or corresponding indications, the movements of the actuation elements "forwards and backwards" can be controlled, and a third control element can control the movement "clockwise or anticlockwise rotation".

It will be appreciated that the aforementioned features and the features still to be explained below can be used not only in the cited combination but also in other combinations or singly, without departing from the scope of the present invention.

BRIEF DESCRIPTION OF THE DRAWING

The invention is described and explained in more detail below on the basis of a number of selected illustrative embodiments and with reference to the attached drawings, in which.

DETAILED DESCRIPTION OF PREFERRED EMBODIMENTS

Figure 1:
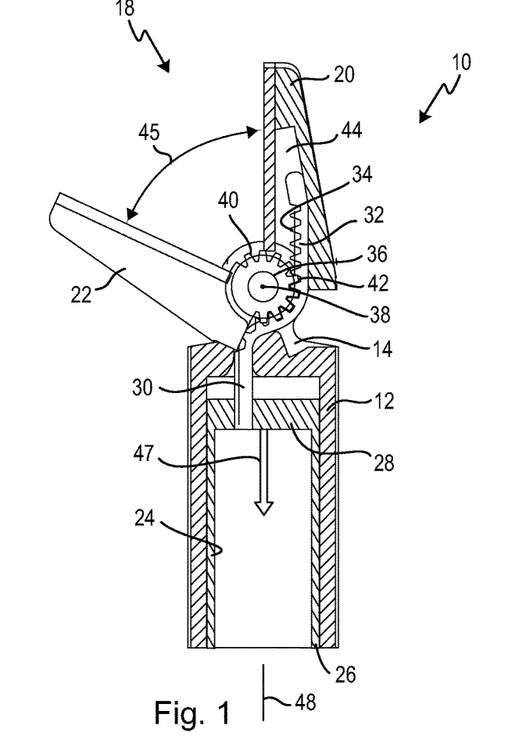
FIG. 1 shows a partially sectioned side view of a first illustrative embodiment of a medical instrument, in the area of the distal end thereof with the jaw head, specifically with a stationary jaw part and with a jaw part pivoted relative to the latter.
Figure 2:
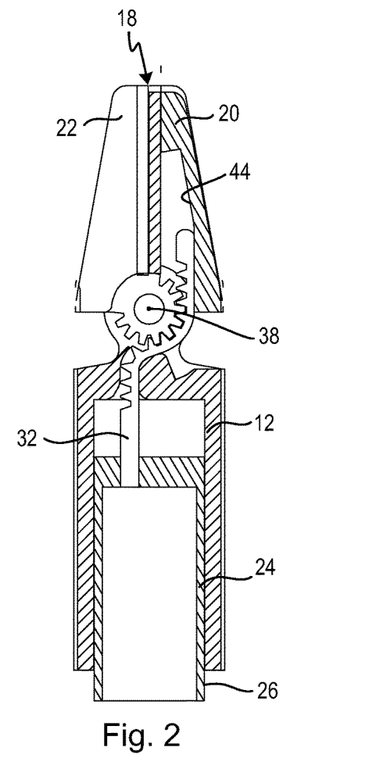
FIG. 2 shows a view corresponding to the view in FIG. 1 but with the jaw parts closed.
Figure 3:
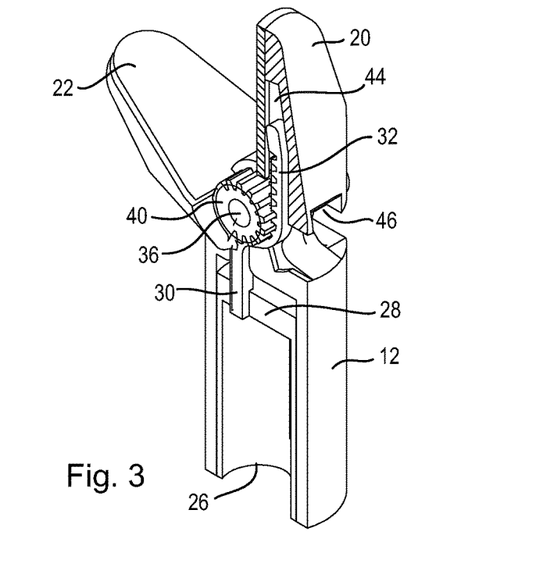
FIG. 3 shows a perspective view of the position in FIG. 1, with the stationary jaw part in cross section.

FIGS. 1 to 3 show a first illustrative embodiment of a medical instrument, which is designated in its entirety by reference number 10.

Only the distal end portion of the medical instrument 10 is shown in each of FIGS. 1 to 3, that is to say the end of the shaft 12 and the jaw head 18 secured thereon. The underlying principle of the function of the present invention will be explained using these figures.

As has been mentioned, the medical instrument 10 has a rigid elongate hollow shaft 12, on the distal end 14 of which a jaw head 18 is secured.

The jaw head 18 has a stationary jaw part 20 and a jaw part 22 pivotable relative to the latter. An actuation element 24 in the form of a tubular body 26 is accommodated in the interior of the shaft 12. The external diameter of the tubular body 26 corresponds approximately to the clear internal diameter of the shaft 12, such that the actuation element 24 is movable axially to and fro in the interior of the shaft 12 and is guided by the latter. The distal end 28 of the tubular body 26 is closed and carries a distal end portion 30 in the form of a belt 32. The belt 32 has a toothing 34 on one side.

The belt 32 is produced from a flexurally elastic material, for example a plastic, a spring steel or an elastic alloy, for example Nitinol.

The pivotable jaw part 22 is mounted on the jaw head 18 so as to be pivotable about a journal 36, the central longitudinal axis 38 thereof extending transversely with respect to the longitudinal axis 48 of the shaft 12. A toothed wheel 40, which has an external toothing 42, is mounted on the journal 36.

The toothing 34 of the belt 32 and the external toothing 42 of the toothed wheel 40 are matched to each other, such that these two parts can mesh with each other. The tooth profile can be as shown, although rounder, shallower or broader teeth can also be present. A width of the belt 32 corresponds to the thickness of the toothed wheel 40.

It is important that this meshing engagement allows forces to be transmitted that are sufficient to move the pivotable jaw part 22 and to transmit such forces as to be able to separate a piece of tissue, even cartilage, held between the jaw parts 20 and 22. The size and the diameter of the toothed wheel 40 and therefore the distance of the meshing engagement from the rotation axis 38 determine the torque of the force trans-mission and must be sufficiently great to be able to exert and transmit precisely these forces.

A hollow space 44, which has a proximal opening 46, is formed in the interior of the stationary jaw part 20.

The opening 46 and the hollow space 44 are designed such that the belt 32 with its toothing 34 can be driven in and out of the hollow space 44 via the opening 46.

The toothed wheel 40 sits on the journal 36, which is connected to the pivotable jaw part 22. However, the arrangement of toothed wheel 40 and belt 32 is such that the distal end portion 30 of the belt 32 can be driven in and out of the hollow space 44 in the other, i.e. the stationary, jaw part 20. Therefore, the belt 32 loops round the toothed wheel 40 opposite the pivotable jaw part 22.

FIG. 2 shows a position with closed jaw parts 20 and 22, and the jaw head 18, seen as a whole, is oriented in the longitudinal extent of the shaft 12.

In this "basic position", the toothing 34 loops round the toothed wheel 40, specifically in such a way that a distally protruding end area is driven into the hollow space 44, but with some of the teeth still lying in the proximal direction from the toothed wheel.

If the actuation element 24 is moved in the distal direction starting from the "basic position" shown in FIG. 2, the belt 32 with its toothing 34 is pushed in the direction of the hollow space 44 in the stationary jaw part 20. The toothed wheel 40 is rotated anticlockwise about the axis 38.

The pivotable jaw part 22 is correspondingly pivoted, i.e. opened, as is shown in FIG. 1.

When the actuation element 24 is moved in the opposite direction, as is shown by the arrow 47, the pivotable jaw part 22 closes. The latter is therefore pivotable to and fro across a certain range, as is indicated by the double arrow 45.

In the opened position shown in FIG. 1, a piece of tissue or cartilage that is to be grasped or separated can now be brought between the opened jaw parts 20 and 22.

By moving the actuation element 24 in the proximal direction, as is indicated by the arrow 47, the belt 32 is "pulled", and the latter then also moves in the proximal direction, as a result of which the toothed wheel 40 is then moved clockwise and the pivotable second jaw part 22 is placed onto the stationary jaw part 20. The state shown in FIG. 2 is once again reached in the end position.

This "pulling" on the belt 32 when closing the pivotable jaw part 22 has the advantage that tensile forces can be transmitted much better by a belt of this kind, without deformations, than a sliding movement.

This arrangement is expedient since the considerable forces for separating cartilage, for example, have to be applied during this closure, i.e. this "pulling".

Particularly in designs with a stationary jaw part, the latter is sometimes larger, more stable and more voluminous than the pivotable movable jaw part, such that the provision of the hollow space in this stationary jaw part is expedient.

However, if both jaw parts 20 and 22 are of the same design, it is of course also possible in principle to allow the belt 32 to run into a hollow space on the movable jaw part 22.

To do this here, for example, the belt 32 would simply have to be turned 180° about its longitudinal axis, such that it does not then run along the toothed wheel 40 on the right-hand side, as shown here, but instead on the other side, that is to say in the opposite direction.

A control element is then present at the proximal end (not shown here) of the shaft 12 and controls the linear movement of the actuation element 24.

This can be, for example, a movable grip part of a scissor part, as is customary in instrument design, wherein the actuation element 24 is then connected to the movable grip part.

A second illustrative embodiment of a medical instrument according to the invention is described in connection with FIGS. 4 to 10 and is designated in its entirety by reference number 50. FIGS. 4 to 9 show cross sections and situations which are comparable to the cross sections in FIGS. 1 and 2.

Figure 4:
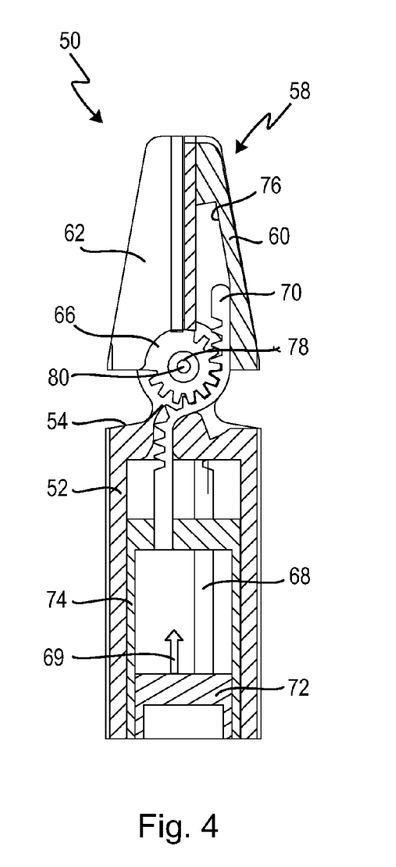
FIG. 4 shows a longitudinal section through a second illustrative embodiment of a medical instrument with two movable jaw parts.

In principle, the medical instrument 50 also has a shaft 52, on the distal end 54 of which a jaw head 58 is arranged.

The jaw head 58 has a first jaw part 60 and a second jaw part 62, which are both pivotable.

For this purpose, the first jaw part 60 is connected to a first toothed wheel, which is not visible in these views, since it is in each case concealed behind the second toothed wheel 66.

The first toothed wheel meshes with a first toothed belt 68, the second toothed wheel 66 with a second toothed belt 70.

The first toothed belt 68 is connected to a tubular first actuation element 72, which is arranged in the interior of a likewise tubular second actuation element 74, which in turn lies and is guided in the interior of the shaft 52, as has been described above in connection with the actuation element 24.

As will be seen from FIG. 4, the distal end area of the second toothed belt 70 extends into a hollow space 76 in the first jaw part 60.

Accordingly, the first toothed belt 68 behaves conversely, its distal end area extending into a hollow space (not shown here) in the second jaw part 62.

The second toothed belt 70 meshes with the second toothed wheel 66, which moves the second jaw part 62, but, as has been described above, runs into the hollow space 76 in the first jaw part 60.

Both toothed wheels extend on the same axis and are each mounted on two journals 78 and 80 pushed coaxially one into the other, such that they can be rotated relative to each other.

FIG. 4 shows once again a basic position comparable to the position in FIG. 2.

Figure 5:
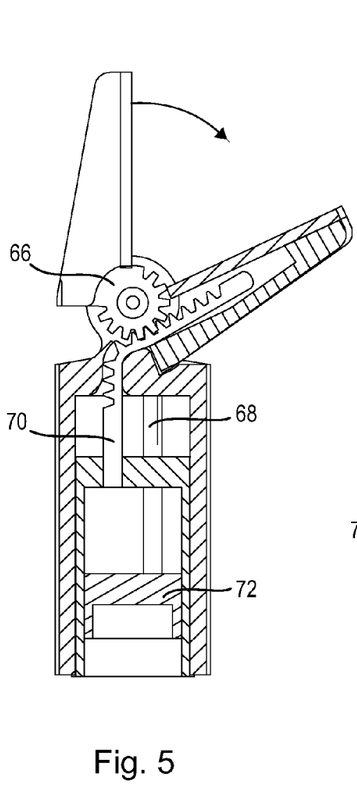
FIG. 5 shows a view comparable to FIG. 4, with one jaw part pivoted.

If the first actuation element 72 is now moved in the distal direction, as is indicated by an arrow 69, its first toothed belt 68 pivots the first jaw part 60 towards the right in the view in FIG. 5.

The second toothed belt 70, which is of course not moved axially during this movement, nonetheless has the possibility of moving slightly into the hollow space 76 of the first jaw part 60, since it is carried along by this jaw part 60.

The second toothed wheel 66 does not rotate here.

Figure 6:
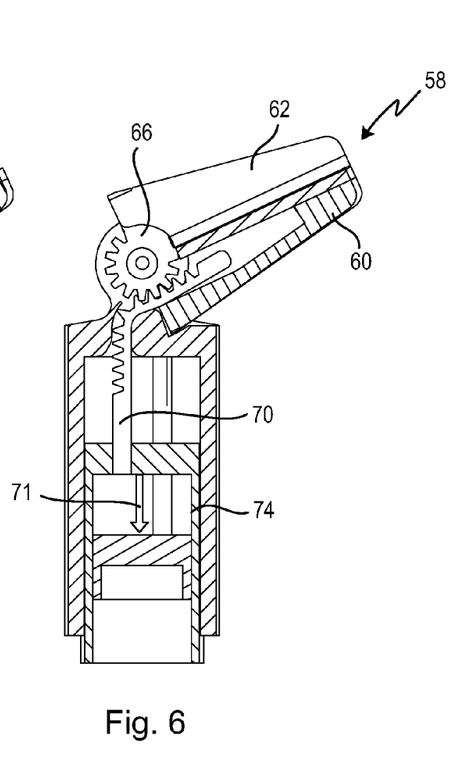
FIG. 6 shows a view comparable to FIG. 4, with both jaw parts pivoted to the right.

If, starting from the position in FIG. 5, the second actuation element 74 is now moved in the proximal direction, as is indicated by an arrow 71 in FIG. 6, the second toothed belt 70 is also pulled in the proximal direction, whereby the second toothed wheel 66 rotates in the clockwise direction and the second jaw part 62 thus pivots in the clockwise direction, for example to such an extent that it lies on the first jaw part 60, as is shown in FIG. 6.

A piece of tissue or cartilage brought between the opened jaw parts 60 and 62 in the view in FIG. 5 can thus be grasped or separated.

Figure 7:
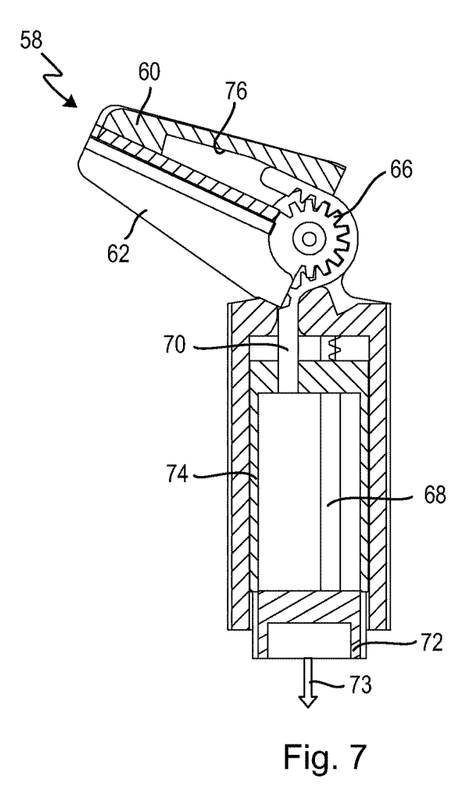
FIG. 7 shows a view corresponding to FIG. 6, with both jaw parts lying together and pivoted in the opposite direction, i.e. to the left.

FIG. 7 shows a situation in which the jaw parts 60 and 62 are pivoted to the maximum extent to the left, i.e. the maximum position of pivoting counter to that in the view in FIG. 6.

For this purpose, the second toothed belt 70 was advanced in the distal direction by the second actuation element 74, and the second toothed wheel 66 thus rotated anticlockwise, until the second jaw part 62 has reached the pivoting position shown in FIG. 7. The first actuation element 72 moved the first toothed belt 68 so far in the proximal direction, as is shown by the arrow 73 in FIG. 7, that the first jaw part 60 was pivoted to the left until it lies on the second jaw part 62. Thus, the jaw part 58, in the closed state, can be pivoted to and fro between the extreme positions in FIG. 6 and FIG. 7.

Figure 8:
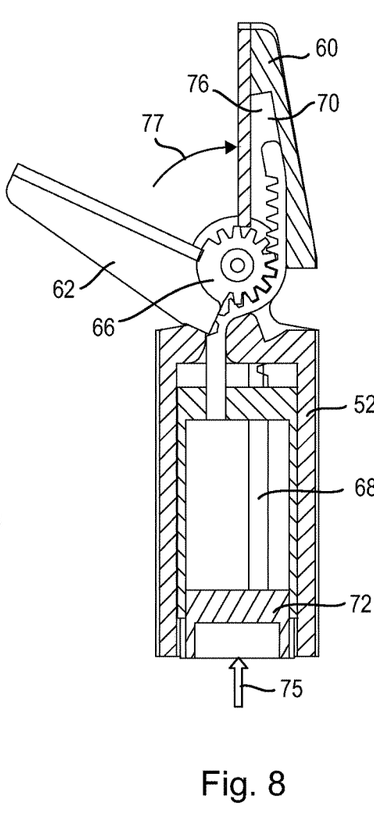
FIG. 8 shows a view comparable to FIG. 5, with one of the jaw parts oriented rectilinearly with the shaft and one of them pivoted to the left.

FIG. 8 shows a situation in which the first jaw part 60 has been brought into a rectilinear orientation with the shaft 52.

For this purpose, the first toothed belt 68 was moved so far in the distal direction by the first actuation element 72 that the rectilinear orientation is achieved. This is indicated by an arrow 75 in FIG. 8.

The second jaw part 62 and the second toothed wheel 66 rigidly connected thereto do not move here.

Only the toothing of the second toothed belt 70 has detached itself slightly from the loop around the second toothed wheel 66 during the adjustment of the first jaw part 60, as can be seen from the change from FIG. 7 to FIG. 8.

Figure 9:
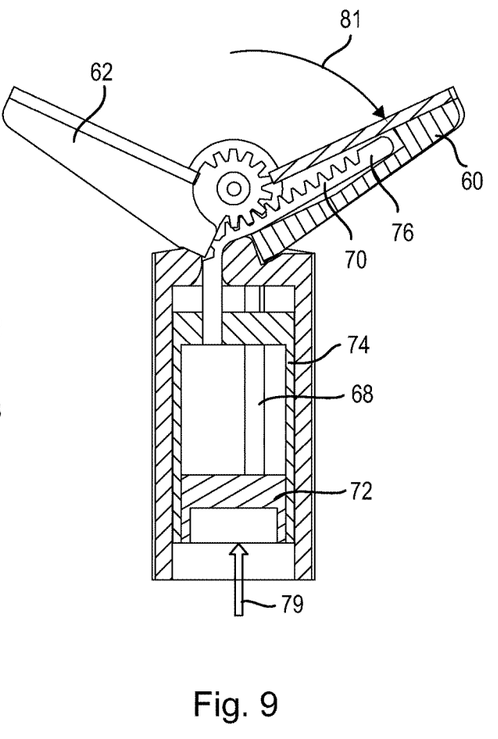
FIG. 9 shows a view comparable to FIG. 4, with both jaw parts pivoted to the maximum extent in opposite directions.

If the first actuation element 72 is now moved further in the distal direction, as is shown by the arrow 79 in FIG. 9, the first jaw part 60 is pivoted still further in the same direction, towards the right in the view in FIG. 9, as is shown by the arrow 81, until the maximum opening position of the two jaw parts 60 and 62 is reached.

If, for example, the jaw parts 60 and 62 are now to be closed by moving the second jaw part 62 towards the first jaw part 60, the second actuation element 74 has to be moved in the proximal direction and the second toothed belt 70 thereby pulled out of the hollow space 76.

This can be done until the position shown in FIG. 6 is reached again.

It will be clear from this that the mobility of the two jaw parts 60 and 62 affords the operator many possibilities of either pivoting the entire jaw head 58 with closed jaw parts 60 and 62 (for example transition to FIG. 6 or FIG. 7) or of opening and closing the jaw parts 60, 62 in any desired positions and any desired orientation of the jaw head 58, as is shown for example in FIG. 5, FIG. 8 and FIG. 9. The operator is thus provided with many degrees of freedom as regards the orientation of the jaw head 58 for grasping or separating pieces of tissue or cartilage.

Figure 10:
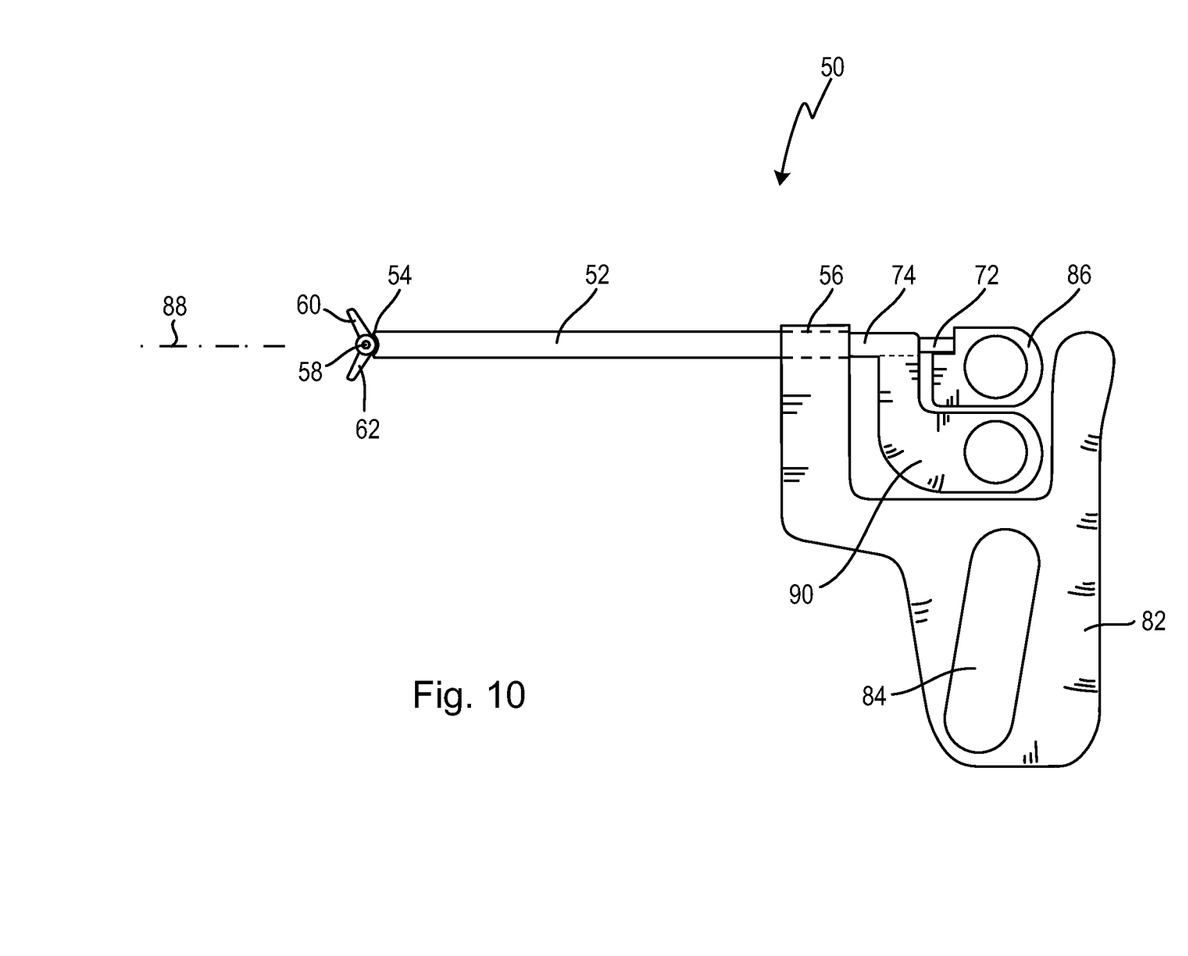
FIG. 10 shows a side view of the entire medical instrument of the second illustrative embodiment with a manual drive.

FIG. 10 shows a side view of the medical instrument 50 in its entirety. At the proximal end 56 of the shaft 52, a handle 82 is mounted rigidly on the latter.

The handle 82 is shaped like a pistol grip and is provided with an elongate finger eyelet 84.

The above-described tubular second actuation element 74, at the proximal end of which a second grip part 90 is mounted, is pushed into the shaft 52.

The likewise tubular body of the first actuation element 72 is pushed into the tubular body of the second actuation element 74. The proximal end of the first actuation element 72 is connected to a first grip part 86.

The two grip parts 86 and 90 are provided with finger eyelets (not shown here). Fingers of a hand that has taken hold of the medical instrument 50 via the handle 82 can then be pushed into these finger eyelets.

The linear movements along the shaft axis 88, which have been described in detail above in connection with FIGS. 4 to 9, can now be controlled using these grip parts, in order thereby to move the jaw parts 60 and 62 of the jaw head 58. The handle 82 can be rotated about the shaft axis 88 around the respective other grip parts.

Figure 11:
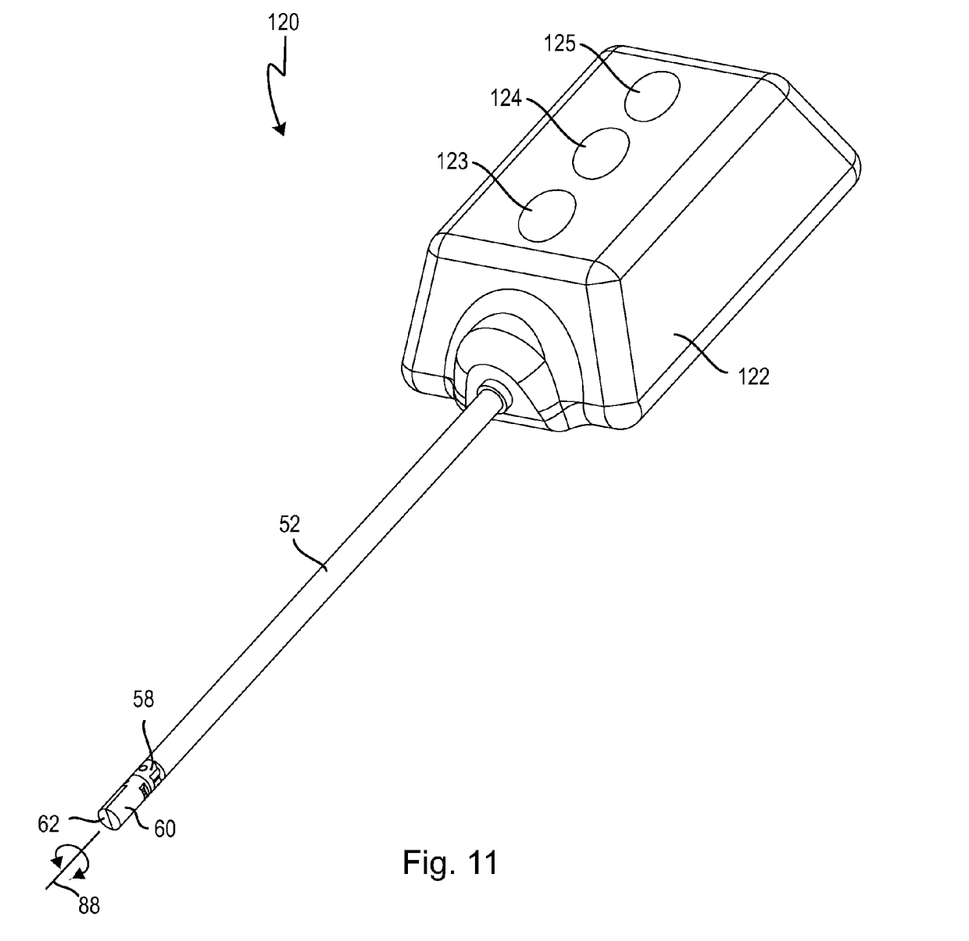
FIG. 11 shows a further illustrative embodiment of a medical instrument, with a motorized drive.

FIG. 11 shows a further illustrative embodiment of such a medical instrument 120, in which motorized drives 122 are arranged at the proximal end.

The shaft 52, the jaw head 58 and the jaw parts 60 and 62 are in principle of the same design as described above.

The proximal ends of the first and second actuation elements 72, 74 are each connected to axial actuating drives which, for example, can be controlled, i.e. actuated, by the control elements 123 and 124.

These control elements 123, 124 can be knobs or toggle switches, by which the movements in the distal direction and proximal direction can be controlled independently of each other, in order to open and close the jaw parts 60 and 62 or thereby also pivot the jaw head 58 as a whole.

The control element 125 can control the rotation movement, i.e. the rotation of the assembly about the shaft axis. For this purpose, a rotary drive is mounted on one of the actuation elements.

A medical instrument is described, with a shaft 12, 52 which has a distal end 14, 54 and a proximal end 16, 56, with a jaw head 18, 58, which is arranged on the distal end 14, 54 and has two jaw parts 20, 22; 60, 62, of which at least one 22; 60, 62 is pivotable, with at least one actuation element 24; 72, 74 for pivoting the pivotable jaw part 22; 60, 62, wherein the pivotable jaw part 22; 60, 62 is pivotable about an axis 38, 80 and has at least one toothed wheel portion 40; 64, 66, which meshes with a toothing 34; 68, 70 on the distal end portion 30 of the actuation element 24; 72, 74, in such a way that an axial movement of the actuation element 24; 72, 74 causes a pivoting of a jaw part 22; 60, 62, and with control elements which are arranged at the proximal end of the shaft 12, 52 and are used for controlling the movement of the at least one actuation element 24; 72, 74, characterized in that the distal end portion 30 of the at least one actuation element 24; 72, 74 is flexible, and that a flexible end portion 30 can be driven in and out of a hollow space 44; 76 of a jaw part 20, 22; 60, 62 in the distal direction from the toothed wheel portion 40; 64, 66.

LIST OF REFERENCE SIGNS 10 medical instrument
12 shaft
14 distal end
16 proximal end
18 jaw head
20 stationary jaw part
22 pivotable jaw part
24 actuation element
26 tubular body
28 end
30 distal end portion
32 belt
34 toothing
36 journal
38 axis
40 toothed wheel
42 external toothing
44 hollow space
45 arrow
46 opening
47 arrow
48 longitudinal axis
50 medical instrument
52 shaft
54 distal end
56 proximal end
58 jaw head
60 first jaw part
62 second jaw part 66 second toothed wheel
68 first toothed belt
69 arrow
70 second toothed belt
71 arrow
72 first actuation element
73 arrow
74 second actuation element
75 arrow
76 hollow space
77 arrow
78 first journal
80 second journal
82 handle
84 finger eyelet
86 first grip part
88 shaft axis
90 second grip part
120 medical instrument
122 drive
123 control element
124 control element
125 control element

What is claimed is:

1. A medical instrument, comprising:
    a shaft having a distal end, a proximal end and a longitudinal shaft axis;
    a jaw head arranged on said distal end of said shaft;
    said jaw head having two jaw parts, at least one of said two jaw parts being pivotable about a pivot axis extending transversely to said shaft axis, said at least one pivotable jaw part having a wheel portion mounted about said pivot axis, said wheel portion having a toothing;
    at least one actuation element for pivoting said at least one pivotable jaw part, said at least one actuation element having a distal end portion provided with a toothing, said toothing of said at least one actuation element meshes with said toothing of said wheel portion in such a way that an axial movement of said at least one actuation element along said longitudinal axis of said shaft pivots said pivotable jaw part; and
    control elements arranged at said proximal end of said shaft, said control elements controlling a movement of said at least one actuation element;
    wherein said distal end portion of said at least one actuation element provided with said toothing is made flexible;
    wherein at least one of said two jaw parts comprises therein a hollow space arranged distally to said pivot axis; and
    wherein said flexible distal end portion of said at least one actuation element comes in or comes out of said hollow space when moving said at least one actuation element along said shaft axis distally and proximally, respectively, wherein said flexible distal end portion of said at least one actuation element is flexed as said at least one pivotable jaw part is pivoted.

2. The medical instrument of claim 1, wherein said hollow space is arranged within said at least one jaw part and has a proximal opening through which said flexible distal end portion of said at least one actuation element having said toothing can be driven in and out of the hollow space in said at least one jaw part.

3. The medical instrument of claim 2, wherein said hollow space completely encloses said flexible distal end portion of said at least one actuation element, except for the proximal opening.

4. The medical instrument of claim 1, wherein said flexible distal end portion can be driven in and out of said hollow space of that particular jaw part that can be pivoted by said at least one actuation element having said flexible toothed end portion.

5. The medical instrument of claim 1, wherein said flexible distal end portion can be driven in and out of a hollow space formed in another one of said two jaw parts that is not arranged to be pivoted by said distal end portion.

6. The medical instrument of claim 1, wherein said jaw head has a stationary jaw part and a pivotable jaw part, and wherein said hollow space being formed in said stationary jaw part.

7. The medical instrument of claim 1, wherein said toothed wheel portion is formed on a toothed wheel with an external toothing, which toothed wheel is mounted on a journal about which said jaw part is pivotable.

8. The medical instrument of claim 7, wherein said toothed wheel is mounted in such a way that it is integrated as fully as possible within said jaw part.

9. The medical instrument of claim 1, wherein said jaw head has two pivotable jaw parts, each of said two jaw parts is connected to a separate actuation element, such that these two jaw parts can be opened and closed individually and can be moved in the same direction thereby pivoting the entire jaw head respectively.

10. The medical instrument of claim 9, wherein each of said two pivotable jaw parts being provided with a toothed wheel, and wherein said two toothed wheels each being pivotable about a same pivot axis.

11. The medical instrument of claim 9, wherein said two actuation elements are accommodated in said shaft coaxially with respect to each other.

12. The medical instrument of claim 11, wherein said two actuation elements are designed as two tubular bodies which are inserted one to another within said shaft, and said flexible toothed distal end portions protrude from distal ends of said tubular bodies.

13. The medical instrument of claim 1, wherein each of said at least one actuation element is connected at its proximal end to a control element.

14. The medical instrument of claim 13, wherein a handle containing said control elements is arranged at said proximal end of said shaft.

15. The medical instrument of claim 14, wherein said handle is provided with grip parts having finger eyelets.

16. The medical instrument of claim 1, wherein said at least one actuation element is accommodated in said shaft in such a way that they are rotatable about said longitudinal axis of said shaft.

17. The medical instrument of claim 1, wherein said control elements and said shaft are rotatable relative to each other about said shaft axis.

18. The medical instrument of claim 1, wherein said control elements are designed as motorized drives for moving said at least one actuation element axially to and fro within the shaft.

19. The medical instrument of claim 18, wherein said motorized drive can rotate said at least one actuation element within said shaft.

20. A medical instrument, comprising:
    a shaft having a distal end, a proximal end and a longitudinal shaft axis;

a jaw head arranged on said distal end of said shaft;
said jaw head having two jaw parts, at least one of said two jaw parts being pivotable about a pivot axis extending transversely to said shaft axis, said at least one pivotable jaw part having a wheel portion mounted about said pivot axis, said wheel portion having a toothing;
at least one actuation element for pivoting said at least one pivotable jaw part, said at least one actuation element having a distal end portion provided with a toothing, said toothing of said at least one actuation element meshes with said toothing of said wheel portion in such a way that an axial movement of said at least one actuation element along said longitudinal axis of said shaft pivots said pivotable jaw part; and
control elements arranged at said proximal end of said shaft, said control elements controlling a movement of said at least one actuation element;
wherein said distal end portion of said at least one actuation element provided with said toothing is made flexible;
wherein at least one of said two jaw parts comprises therein a hollow space arranged distally to said pivot axis;
wherein said flexible distal end portion of said at least one actuation element is inserted in or pulled out of said hollow space when moving said at least one actuation element along said shaft axis distally and proximally, respectively; and
wherein said hollow space is formed within said at least one pivotable jaw part so that said flexible distal end portion of said at least one actuation element is flexed as said at least one pivotable jaw part is pivoted.

21. A medical instrument, comprising:
a shaft having a distal end, a proximal end and a longitudinal shaft axis;
a jaw head arranged on said distal end of said shaft;
said jaw head having a first pivotable jaw part and a second pivotable jaw part,
said first pivotable jaw part having a first wheel portion comprising a toothing;
said second pivotable jaw part having a second wheel portion comprising a toothing;
a first actuation element for pivoting said first pivotable jaw part, said first actuation element having a first flexible distal end portion provided with a toothing;
a second actuation element for pivoting said second pivotable jaw part, said second actuation element having a second flexible distal end portion provided with a toothing; and
control elements arranged at said proximal end of said shaft, said control elements controlling a movement of said first actuation element and said second actuation element;
wherein said toothing of said first actuation element meshes with said toothing of said first wheel portion in such a way that an axial movement of said first actuation element along said longitudinal axis of said shaft pivots said first pivotable jaw part;
wherein said toothing of said second actuation element meshes with said toothing of said second wheel portion in such a way that an axial movement of said second actuation element along said longitudinal axis of said shaft pivots said second pivotable jaw part;
wherein each of said two jaw parts comprises therein a hollow space;
wherein said flexible distal end portion of said first actuation element engages or disengages from said hollow space of said second jaw part when said first actuation element is actuated to pivot said first jaw part; and
wherein said flexible distal end portion of said second actuation element engages or disengages from said hollow space of said first jaw part when said first actuation element is actuated to pivot said second jaw part, wherein said flexible distal end portion of said first actuation element and said flexible distal end portion of said second actuation element are flexed as said first jaw part and said second jaw part are pivoted, respectively.

* * * * *